US00PP15009P3

(12) United States Plant Patent
Utecht

(10) Patent No.: US PP15,009 P2
(45) Date of Patent: Jul. 13, 2004

(54) GERANIUM PLANT NAMED 'FISAQUA'

(50) Latin Name: *Pelargonium zonale*
Varietal Denomination: Fisaqua

(75) Inventor: Angelika Utecht, Montabaur (DE)

(73) Assignee: Florfis AG, Binningen (CH)

( * ) Notice: Subject to any disclaimer, the term of this patent is extended or adjusted under 35 U.S.C. 154(b) by 0 days.

(21) Appl. No.: 10/715,544

(22) Filed: Nov. 19, 2003

(65) Prior Publication Data

US 2004/0117887 P1 Jun. 17, 2004

(30) Foreign Application Priority Data

Dec. 12, 2002 (DE) ..... PEL 1880
Dec. 23, 2002 (CA) ..... PBR 02-3401

(51) Int. Cl.[7] ..... A01H 5/00
(52) U.S. Cl. ..... Plt./329
(58) Field of Search ..... Plt./325, 327, 328, Plt./329

*Primary Examiner*—Kent Bell
(74) *Attorney, Agent, or Firm*—Foley & Lardner LLP

(57) ABSTRACT

A new and distinct cultivar of geranium plant named 'Fisaqua', particularly characterized by the combined features of light pink to light rose colored, cup-shaped flowers, medium green foliage with weak zonation, and medium over sized plant habit.

1 Drawing Sheet

Genus and species of the plant claimed: Hybrid of *Pelargonium zonale* L'Héritier.
Variety denomination: 'Fisaqua'.

BACKGROUND OF THE INVENTION

The present invention comprises a new and distinct cultivar of geranium, botanically known as *Pelargonium zonale,* and hereinafter referred to by the cultivar name 'Fisaqua'.

'Fisaqua' is a product of a planned breeding program which had the objective of creating new zonal geranium cultivars with light pink flower color, with markings or without, deep green foliage, and medium to vigorous growth habit.

'Fisaqua' originated from a hybridization made by the inventor, Angelika Utecht, in a controlled breeding program in Hillscheid, Germany, in 1996. The female parent was the patented variety 'Fisbravo' (U.S. Plant Pat. No. 9,765), having light bluish-pink flowers with distinct red markings, dark green foliage and fairly compact plant habit. The male parent of 'Fisaqua' was the unpatented variety 'Gomera', characterized by bluish-pink flowers with red markings on petals, medium green foliage with weak zonation, and medium sized plant habit.

'Fisaqua' was selected as one flowering plant within the progeny of the stated cross by Angelika Utecht in 1997 in a controlled environment in Moncarapacho, Portugal.

The first act of asexual reproduction of 'Fisaqua' was accomplished when vegetative cuttings were taken from the initial selection in the fall of 1997 in a controlled environment in Moncarapacho, Portugal, by, or under the supervision of, Angelika Utecht.

Horticultural examination of plants grown from cuttings of the plant initiated in May, 1998, in Hillscheid, Federal Republic of Germany, and continuing thereafter, has demonstrated that the combination of characteristics as herein disclosed for 'Fisaqua' are firmly fixed and are retained through successive generations of asexual reproduction.

'Fisaqua' has not been observed under all possible environmental conditions. The phenotype may vary significantly with variations in environment such as temperature, light intensity and day length.

BRIEF SUMMARY OF THE INVENTION

The following observations, measurements, and comparisons describe plants grown in Hillscheid, Germany, under greenhouse conditions which approximate those generally used in commercial practice.

The following traits have been repeatedly observed and are determined to be basic characteristics of 'Fisaqua' in combination distinguish this geranium as a new and distinct cultivar:

1. Light pink, rose-edged, open, semi-double flowers;
2. Big, round inflorescences, on long peduncles;
3. Medium green foliage with weak zonation;
4. Medium growth, low, rounded plant habit, and
5. Medium to somewhat late spring flowering response.

Of the many commercial cultivars known to the present inventor, the most similar in comparison to 'Fisaqua' is the unpatented, commercial variety 'Goesta', the parental variety 'Gomera', and 'Designer Light Pink' (U.S. Plant Pat. No. 8,552).

In comparison to 'Goesta', 'Fisaqua' has a similar flower color, but somewhat deeper green leaf color, slightly deeper zonation, and somewhat taller plant habit. In comparison to 'Gomera', 'Fisaqua' has a lighter main flower color, and petals lack reddish or deep pink macules. In comparison to 'Designer Light Pink', 'Fisaqua' has a somewhat deeper and more variable pink main flower color, while the main flower color of 'Designer Light Pink' is a uniform, light-pink. Furthermore, the foliage of 'Fisaqua' appears somewhat deeper green, and plant habit is not quite as tall as that of 'Designer Light Pink'.

BRIEF DESCRIPTION OF THE DRAWING

The accompanying photographic drawing shows typical flower and foliage characteristics of 'Fisaqua' with colors being as true as possible with an illustration of this type. The photographic drawing shows a flowering potted plant of 'Fisaqua'.

DETAILED BOTANICAL DESCRIPTION

The measurements were taken in Hillscheid, Germany, in mid May, 11 weeks after planting of rooted cuttings. The plants were growing in 14 cm pots, they had not been pinched.

In the following description color references are made to The Royal Horticultural Society Color Chart. The color values were determined indoors from plants growing in a green-house in May, 2003, in Hillscheid, Germany.

INFLORESCENCE

Umbel:
- *Shape.*—Semi-spherical to almost spherical.
- *Average diameter.*—106 mm.
- *Average depth.*—55 mm.
- *Peduncle length.*—232 mm.
- *Peduncle color.*—Light green, RHS 143 B, outdoors a slight tinge of brown may occur, RHS 147 B.
- *Pedicel.*—31 mm in length.
- *Pedicel color.*—Reddish brown, RHS 181 A.
- *Number of flowers per umbel.*—Up to 65.

Corolla:
- *Average diameter.*—55 mm.
- *Form.*—Weakly semi-double type, appears almost as single-type.
- *Shape.*—Round outline, with the upper petals about the same size as the lower petals, flat cup-shape.
- *Number of petals.*—Usually 6.
- *Shape of petals.*—Obovate, base acute, upper end is truncate or rounded, margin is entire.
- *Size of petals.*—Upper petals: 29 mm long, 21 mm wide; lower petals: 25–26 mm long, 24–26 mm wide.
- *Color (general tonality from a distance of three meters).*—Light pink, almost white to light rose.
- *Color of upper petals.*—Mainly RHS 73 B to 73 C; in some parts and especially near margin somewhat deeper pink, RHS 68 B to 68 C.
- *Markings of upper petals.*—A small pink spot and weak pink veins, RHS 68 B.
- *Color of lower petals.*—Between RHS 69 D and RHS 155 D, near margin RHS 68 A to 68 B.
- *Markings of lower petals.*—Weak pink eyes, RHS 68 B, at the base of petals.
- *Color of lower surface of petals.*—Mainly RHS 69 B, near margin RHS 68 A, deep pink colored veins, RHS 68 A.
- *Color of sepals.*—Outer surface: mainly green, RHS 143 B, near base RHS 181 B; inner surface: mainly RHS 143 C, near base RHS 181 C.
- *Number of sepals.*—5.
- *Shape of sepals.*—Linear to lanceolate, acute tip, truncate base, surface with moderate pubescence, margin entire.
- *Size of sepals.*—12–14 mm long, 4 mm wide for the largest upper sepal, 2–3 mm in width for the other sepals.

Bud: (just prior to petals unfolding):
- *Shape.*—Elliptical, relatively narrow.
- *Color of sepals.*—Light green, RHS 143 C.
- *Color of petals.*—RHS 45 B.
- *Length.*—15–16 mm.
- *Width.*—8–9 mm.

Reproductive organs:
- *Androecium.*—7–11 fertile anthers, plenty of pollen, yellow-orange, RHS 32 A, filaments white, RHS 155 D, to light-pink, RHS 52 D.
- *Gynoecium.*—One pistil, pink style, RHS 54 A, stigma 5–6-lobed stigma, reddish, RHS 47 A.
- *Fertility/seed set.*—Not yet observed.

Spring flowering response period: In Hillscheid, Germany, in 2001, plants had on average 0.1 flowers opened 8 weeks after planting of rooted cuttings Outdoor flower production: Continuously and moderately rich flowering, the flower count in 2003 in Hillscheid, Germany, indicated about 1.75 inflorescence per plant in mid May.

Durability: Good stability of flower color, fair rain resistance

Lastingness of the individual flower: About 7–8 days at 18° C., about 15 days for the umbel.

Fragrance: None.

PLANT

Foliage:
- *Shape.*—Kidney shaped, with cordate base, with the gap between the lowest lobes open, apex rounded with weak lobes, distinctly wavy.
- *Margin.*—Bicrenate.
- *Texture.*—Upper surface smooth.
- *Size of leaf.*—118 mm wide, 75 mm long.
- *Color of upper surface.*—Medium green, approximately RHS 137 C to RHS 137 D.
- *Color of zonation.*—Brown, closest to RHS 166 A.
- *Color of lower surface.*—RHS 143 B to RHS 144 B.
- *Petioles.*—Approximately 80–100 mm long, 3 mm in diameter, (light) green in color, approximately RHS 143 A.

General appearance and form:
- *Stem color.*—Light green, RHS 143 B.
- *Internode length.*—15–25 mm.
- *Branching pattern.*—4–5 branches.
- *Size of plants.*—21.0 cm high, 32.5 cm wide, 11-week-old plants, as described, measured from the top of the soil (base of the main stem) to the surface of the foliage canopy, without inflorescences.

I claim:

1. A new and distinct cultivar of geranium plant named 'Fisaqua', as described and illustrated herein.

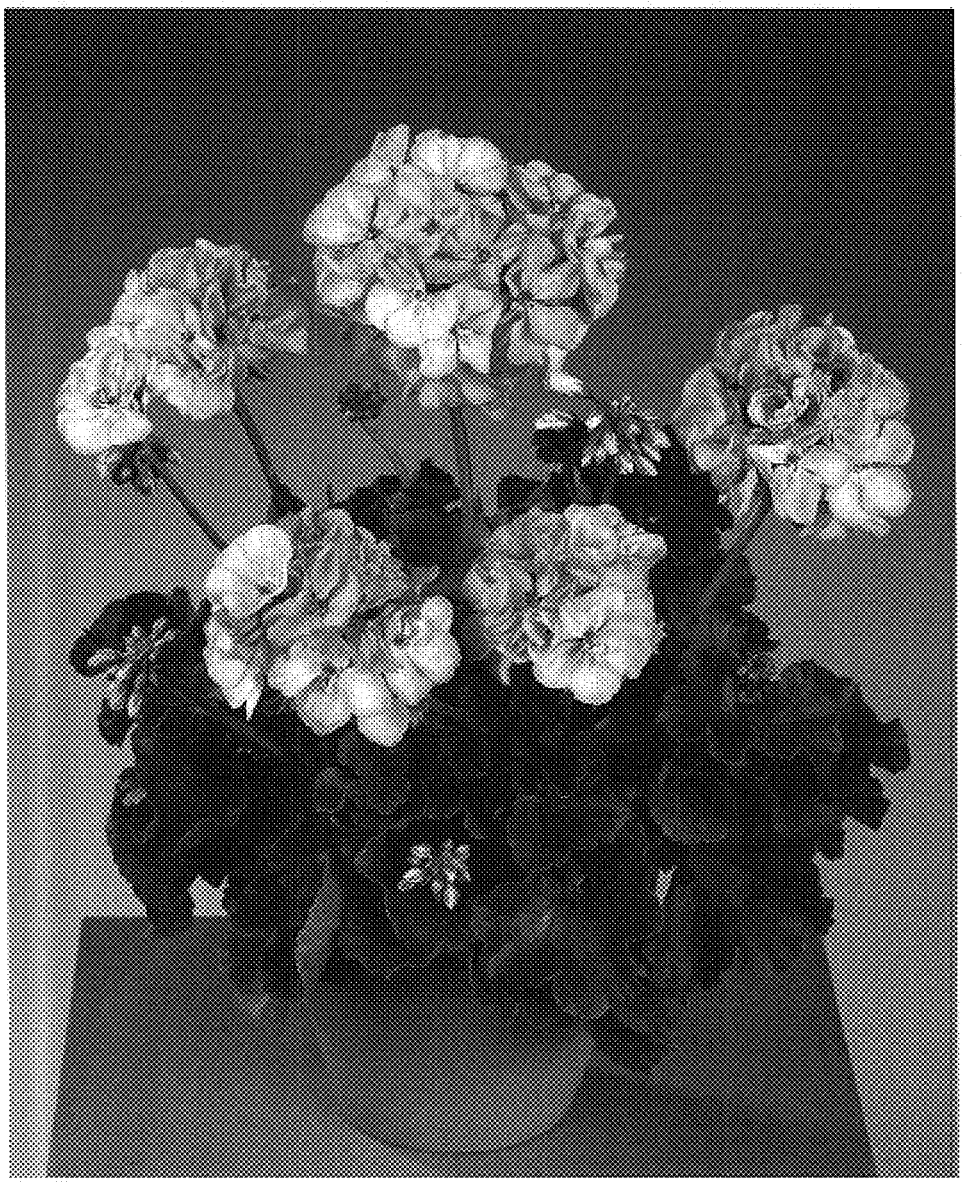

* * * * *